US009434694B2

(12) United States Patent
Doerwald et al.

(10) Patent No.: US 9,434,694 B2
(45) Date of Patent: Sep. 6, 2016

(54) METHOD FOR PREPARATION OF MEDETOMIDINE WITH CHLOROACETONE

(71) Applicant: Lonza Ltd, Visp (CH)

(72) Inventors: Florencio Zaragoza Doerwald, Visp (CH); Anna Kulesza, Ausserberg (CH); Stephan Elzner, Brig-Glis (CH); Robert Bujok, Warsaw (PL); Zbigniew Wrobel, Warsaw (PL); Krzysztof Wojciechowski, Warsaw (PL)

(73) Assignee: Lonza Ltd., Visp (CH)

( * ) Notice: Subject to any disclaimer, the term of this patent is extended or adjusted under 35 U.S.C. 154(b) by 0 days.

(21) Appl. No.: 14/813,681

(22) Filed: Jul. 30, 2015

(65) Prior Publication Data

US 2015/0336909 A1 Nov. 26, 2015

Related U.S. Application Data

(62) Division of application No. 14/385,797, filed as application No. PCT/EP2012/072798 on Nov. 15, 2012, now Pat. No. 9,156,793.

(60) Provisional application No. 61/665,510, filed on Jun. 28, 2012.

(30) Foreign Application Priority Data

Jun. 28, 2012 (EP) ..................................... 12174102
Oct. 11, 2012 (EP) ..................................... 12188104
Oct. 22, 2012 (WO) ................. PCT/EP2012/070875
Nov. 14, 2012 (EP) ..................................... 12192625

(51) Int. Cl.
*C07D 263/16* (2006.01)
*C07D 233/58* (2006.01)
*C07D 233/56* (2006.01)

(52) U.S. Cl.
CPC ........... *C07D 233/58* (2013.01); *C07D 233/56* (2013.01); *C07D 263/16* (2013.01)

(58) Field of Classification Search
CPC . C07D 233/58; C07D 233/56; C07D 263/16
USPC ........................................................ 548/225
See application file for complete search history.

(56) References Cited

U.S. PATENT DOCUMENTS

| 4,514,412 | A | 4/1985 | Karjalainen et al. |
| 4,544,664 | A | 10/1985 | Karjalainen et al. |
| 4,621,150 | A | 11/1986 | Hirai et al. |
| 4,639,464 | A | 1/1987 | Karjalainen et al. |
| RE23,400 | E | 4/1987 | Karjalainen et al. |
| 4,826,864 | A | 5/1989 | Karjalainen et al. |
| 6,313,354 | B1 | 11/2001 | Markert et al. |
| 7,902,247 | B2 | 3/2011 | Sinha et al. |
| 7,902,377 | B2 | 3/2011 | Reine et al. |
| 8,735,438 | B2 | 5/2014 | Sinha et al. |
| 2009/0176843 | A1 | 7/2009 | Sinha et al. |
| 2010/0048915 | A1 | 2/2010 | Reine et al. |
| 2011/0077274 | A1 | 3/2011 | Sinha et al. |

FOREIGN PATENT DOCUMENTS

| AU | 4822172 | 5/1974 |
| CN | 101921234 A | 12/2010 |
| DE | 2252080 | 5/1973 |
| EP | 0058047 | 8/1982 |
| EP | 0153692 | 9/1985 |
| EP | 1918282 | 5/2008 |
| GB | 2101114 | 1/1983 |
| GB | 2453982 | 4/2009 |
| JP | S51-100041 | 9/1976 |
| JP | S51-100042 | 9/1976 |
| NL | 7214315 | 5/1973 |
| WO | WO 98/45237 | 10/1998 |
| WO | WO 00/42851 | 7/2000 |
| WO | WO 2009/089132 | 7/2009 |
| WO | WO 2011/070069 | 6/2011 |
| WO | WO 2012/172120 | 12/2012 |
| WO | WO 2013/011155 | 1/2013 |
| WO | WO 2013/011156 | 1/2013 |
| WO | WO 2013/011158 | 1/2013 |

OTHER PUBLICATIONS

De Esch, I., A. Gaffar, W. Menge and H. Timmerman "Synthesis and Histamine H3 Receptor Activity of 4-(n-Alkyl)-1H-imidazoles and 4-(w-Phenylalkyl)-1H-imidazoles" Bioorganic and Medicinal Chemistry (1999), 7(12), pp. 3003-3009.*
EP Application No. 12167135.8 Extended Search Report, Sep. 25, 2012.
PCT/EP2013/070870 International Search Report and Written Opinion, Feb. 1, 2013.
PCT/EP2012/072796 International Search Report and Written Opinion, Feb. 1, 2013.
PCT/EP2012/072796 Written Opinion, Jun. 17, 2014.
PCT/EP2012/072796 International Preliminary Report on Patentability, Sep. 15, 2014.
PCT/EP2012/072797 Written Opinion, Feb. 1, 2013.
PCt/EP2012/072797 International Search Report, Feb. 1, 2013.
PCT/EP2012/072797 International Preliminary Report on Patentability, Apr. 25, 2014.
PCT/EP2012/072798 International Search Report and Written Opinion, Dec. 17, 2012.
PCT/EP2012/072799 International Search Report and Written Opinion, Mar. 20, 2013.
Cordi et al., Efficient Synthesis of (S)-4(5)-[1-2,3-Dimethylphenyl) ethyl] Imidazole Tartrate, the Potent $\alpha_2$ Adrenoreceptor Agonist Dexmedetomidine, Synthetic Communications, 26(8), pp. 1585-1593 (1996).
Huebner et al., Aconite alkaloids. XVI. Staphisine and the hydrocarbon obtained from its dehydrongenation, Journal of Biological Chemistry, vol. 169, pp. 211-220, (1947).
Mukherjee-Muller et al., 176. Säurekatalysierte Umlagerungen von 1,5.Dimethyl-6-methyliden-tricyclo[3.2.1.0  2,7]oct-3-en-8endo-olen, Helvetica Chimica Acta, vol. 60, Fasc. 5, pp. 1758-1780, (1977).
Zhang et al., Ultrasound-Promoted Synthesis of Substituted Phenanthrene-1,4-Quinones ; The Structure of Plectranthon D. Tetrahedron Letters, vol. 23, No. 14, pp. 2153-2156, (1994).

* cited by examiner

*Primary Examiner* — Alicia L Otton
*Assistant Examiner* — Sagar Patel
(74) *Attorney, Agent, or Firm* — Dority & Manning, P.A.

(57) ABSTRACT

The invention discloses a method for the preparation of medetomidine starting from 1-bromo 2,3-dimethylbenzene and chloroacetone.

2 Claims, No Drawings

METHOD FOR PREPARATION OF MEDETOMIDINE WITH CHLOROACETONE

This application is a divisional application of U.S. application Ser. No. 14/385,797 having a filing date of Sep. 17, 2014, which is a national stage entry of International Patent Application No, PCT/EP2012/072798 having a filing date of Nov. 15, 2012, which claims the filing benefit of European Patent Application No. 12192625.7, having a filing date of Nov. 14, 2012, International Patent Application No. PCT/EP2012/070875, having a thin date of Oct. 22, 2012, European Patent Application No. 12188104.9, having a filing date of Oct. 11, 2012, U.S. Provisional Application No. 61/665,510, having a filing date of Jun. 28, 2012, and European Patent Application No. 12174102.9, having a filing date of Jun. 28, 2012, all of which are incorporated herein by reference in their entirety.

The invention discloses a method for the preparation of medetomidine starting from 1-bromo 2,3-dimethylbenzene and chloroacetone.

Medetomidine is the compound of formula (XX) and is an alpha2 adrenergic agonist, which is currently being used as veterinary sedative and analgesic and is evaluated as anesthetic.

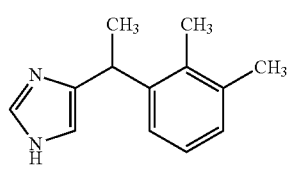

(XX)

Medetomidine is a 4-alkylimidazole. 4-Alkylimidazoles without additional substituents at the nitrogen moiety are usually mixtures of two tautomers. For instance, in the case of medetomidine, two tautomeric forms, represented by compound of formula (XX) and compound of formula (XX-T),

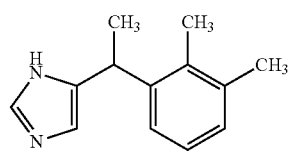

(XX-T)

will usually interconvert if medetomidine is dissolved or in a non-crystalline state. If one of the tautomeric forms prevails or if they are present in equal amounts is dependent on various factors, such as pH, solvent or temperature.

In the text, formula (XX) is used for medetomidine, and is meant to comprise both tautomeric forms as well as their mixture.

US 2010/0048915 A discloses a method for the preparation of medetomidine by reaction of halogenated imidazoles with 2,3-dimethylbenzaldehyde using Grignard reagents. Cordi et al, Synth. Commun. 1996, 26, 1585-1593, discloses the preparation of medetomidine by reaction of 4-imidazolcarboxaldehyde with 2,3-dimethylphenylmagnesium bromide.

WO 00/42851 A discloses the use of medetomidine for inhibition of marine bio fouling on surfaces.

The known methods of preparation of compound of formula (XX) often use protecting groups, for example triphenylmethyl (trityl) residues, which entails high material consumption and the need for protection/deprotection steps. Consequently, these syntheses are long and expensive. Furthermore rather expensive and non-readily available starting materials are used.

There was a need for a synthetic route, which does not need protecting groups, starts with less expensive substrates, avoids large amounts of waste and has satisfying yields.

In the following text, halogen means F, Cl, Br or I, preferably Cl, Br or I;
"alkyl" means linear, branched, cyclic or cyclo alkyl, preferably it means the commonly accepted meaning linear or branched alkyl; if not otherwise stated. Examples of "alkyl" include methyl, ethyl, n-propyl, isopropyl, n-butyl, sec-butyl, tert-butyl, pentyl, hexyl, heptyl, cyclopropyl, cyclobutyl, cyclopentyl, cyclohexyl, cycloheptyl, norbornyl, adamantyl, and the like;
"cyclic alkyl" or "cyclo alkyl" are intended to include cyclo aliphatic, bicyclo aliphatic and tricycle aliphatic residues;
"alkane" means a linear, branched or cyclic alkane, preferably linear or branched alkane;
"alkanol" means a hydroxy alkane, with alkane having the meaning as defined above also with its preferred embodiments;
Ac acetyl;
tBu tertiary butyl;
DBU 1,8-diazabicyclo[5.4.0]undec-7-ene;
DABCO 1,4-diazabicyclo[2.2.2]octane;
DMF N,N-dimethylformamide;
hexanes mixture of isomeric hexanes;
NMP N-methyl-2-pyrrolidone;
OTf trifluoromethanesulfonate, also known as triflate;
sulfamic acid HO—SO$_2$—NH$_2$;
THF tetrahydrofuran;
xylene 1,2-dimethylbenzene, 1,3-dimethylbenzene, 1,4-dimethylbenzene or a mixture thereof;
if not otherwise stated.

Subject of the invention is a method for preparation of compound of formula (XX);

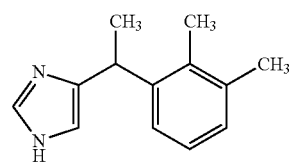

(XX)

the method comprises four steps, the four steps are a step (Q1), a step (Q2), a step (N) and a step (M1);
compound of formula (XX) is prepared in step (M1);
step (M1) comprises a reaction (M1-reac);
reaction (M1-reac) is a reaction between a compound of formula (XXI),

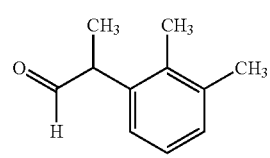

(XXI)

a reagent (M-reag) and a reagent (M-A) in a solvent (M-solv);

reagent (M-reag) is selected from the group consisting of p-toluenesulfonylmethyl isocyanide, trifluoromethanesulfonylmethyl isocyanide, methanesulfonylmethyl isocyanide, benzenesulfonylmethyl isocyanide, 4-acetamidobenzenesulfonylmethyl isocyanide and mixtures thereof;

reagent (M-A) is selected from the group consisting of ammonia, sulfamic acid, p-toluenesulfonamide, benzenesulfonamide, 4-acetamidobenzenesulfonamide, tritylamine, formamide, urea, urotropine, ethyl carbamate, acetamide and mixtures thereof;

solvent (M-solv) is selected from the group consisting of N,N-dimethylformamide, $C_{1-6}$ alkanol, formamide, 1,2-dimethoxyethane, NMP, toluene, acetonitrile, propionitrile, ethyl carbamate, N,N-dimethylacetamide, water, acetamide and mixtures thereof;

compound of formula (XXI) is prepared in step (N);

step (N) comprises a reaction (N-reac);

reaction (N-reac) is a reaction of a compound of formula (XXII) with a catalyst (N-cat);

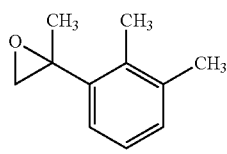

(XXII)

catalyst (N-cat) is selected from the group consisting of acetic acid, formic acid, trifluoroacetic acid, methanesulfonic acid, benzenesulfonic acid, p-toluenesulfonic acid, camphorsulfonic acid, HCl, HBr, $H_2SO_4$, $HNO_3$, $H_3PO_4$, $HClO_4$, $BCl_3$, $BBr_3$, $BF_3OEt_2$, $BF_3SMe_2$, $BF_3THF$, $MgCl_2$, $MgBr_2$, $MgI_2$, $AlCl_3$, $Al(O-C_{1-4}$ alkyl$)_3$, $SnCl_4$, $TiCl_4$, $Ti(O-C_{1-4}$ alkyl$)_4$, $ZrCl_4$, $Bi_2O_3$, $BiCl_3$, $ZnCl_2$, $PbCl_2$, $FeCl_3$, $ScCl_3$, $NiCl_2$, $Yb(OTf)_3$, $Yb(Cl)_3$, $GaCl_3$, $AlBr_3$, $Ce(OTf)_3$, LiCl, $Cu(BF_4)_2$, $Cu(OTf)_2$, $NiBr_2(PPh_3)_2$, $NiBr_2$, $NiCl_2$, $Pd(OAc)_2$, $PdCl_2$, $PtCl_2$, $InCl_3$, acidic inorganic solid substance, acidic ion exchange resin, carbon treated with inorganic acid and mixtures thereof;

step (Q1) comprises a reaction (Q1-reac);

reaction (Q1-reac) is a reaction of compound of formula (XXV) with a reagent (Q1-reag);

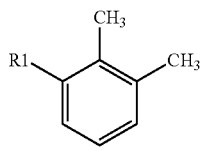

(XXV)

R1 is Br, Cl, or I;

reagent (Q1-reag) is selected from the group consisting of lithium, magnesium, aluminum, zinc, calcium, propylmagnesium chloride, propylmagnesium bromide, butyllithium and mixtures thereof;

step (Q2) comprises a reaction (Q2-reac);

reaction (Q2-reac) is a reaction of the reaction product of reaction (Q1-reac) with chloroacetone;

compound of formula (XXII) is prepared by the reaction (Q2-reac).

Preferably, reagent (M-reag) is selected from the group consisting of p-toluenesulfonylmethyl isocyanide, benzenesulfonylmethyl isocyanide and mixtures thereof;

more preferably, reagent (M-reag) is p-toluenesulfonylmethyl isocyanide.

Preferably, reagent (M-A) is selected from the group consisting of ammonia, sulfamic acid, p-toluenesulfonamide, benzenesulfonamide, 4-acetamidobenzenesulfonamide, tritylamine, formamide and mixtures thereof;

more preferably, reagent (M-A) is selected from the group consisting of ammonia, p-toluenesulfonamide, benzenesulfonamide, formamide, 4-acetamidobenzenesulfonamide, tritylamine and mixtures thereof;

even more preferably, reagent (M-A) is selected from the group consisting of ammonia, p-toluenesulfonamide, formamide, and mixtures thereof;

especially, reagent (M-A) is ammonia or formamide.

Preferably, reaction (M1-reac) is done in the presence of a compound (M-comp), compound (M-comp) is selected from the group consisting of ammonia, tritylamine, NaCN, KCN, piperidine, DBU, DABCO, triethylamine, tributylamine, 4-dimethylaminopyridine, pyridine, tBuOK, tBuONa, $NaHCO_3$, $Na_2CO_3$, $(NH_4)HCO_3$, $(NH_4)_2CO_3$, $KHCO_3$, $K_2CO_3$, NaOAc, KOAc, NaOH, KOH, $Ca(OH)_2$, KF and mixtures thereof;

preferably, compound (M-comp) is selected from the group consisting of ammonia, tritylamine, NaCN, KCN, piperidine, tBuOK, tBuONa, KOH, $K_2CO_3$, $Na_2CO_3$, KF and mixtures thereof;

more preferably, compound (M-comp) is selected from the group consisting of ammonia, NaCN, KCN, piperidine, tBuOK, tBuONa, $K_2CO_3$, $Na_2CO_3$, KF and mixtures thereof;

even more preferably, compound (M-comp) is selected from the group consisting of ammonia, NaCN, $K_2CO_3$, tBuOK, tBuONa, $Na_2CO_3$ and mixtures thereof;

especially, compound (M-comp) is selected from the group consisting of ammonia, NaCN, tBuOK, tBuONa, $K_2CO_3$, $Na_2CO_3$ and mixtures thereof;

more especially, compound (M-comp) is $K_2CO_3$, $Na_2CO_3$, NaCN or ammonia;

even more especially, compound (M-comp) is $Na_2CO_3$, NaCN or ammonia.

Preferably, solvent (M-solv) is selected from the group consisting of N,N-dimethylformamide, methanol, ethanol, n-propanol, isopropanol, butanol, pentanol, hexanol, water, formamide, 1,2-dimethoxyethane, NMP, toluene, acetonitrile, propionitrile, ethyl carbamate, N,N-dimethylacetamide, acetamide and mixtures thereof;

more preferably, solvent (M-solv) is selected from the group consisting of N,N-dimethylformamide, methanol, ethanol, ethyl carbamate, formamide, acetamide and mixture thereof.

The reagent (M-A) can be used as such or in form of a solution in a solvent (M-A). Solvent (M-A) is identical or different from solvent (M-solv), preferably identical, and comprises the same group of solvents as solvent (M-solv), also with respect to all of the preferred embodiments of solvent (M-solv).

When reagent (M-A) is ammonia, then reagent (M-A) is preferably used in form of a solution, preferably in form of a solution in methanol or ethanol.

In case of ethyl carbamate, formamide and acetamide, reagent (M-A) can be identical with solvent (M-solv) and can be used as solvent (M-solv).

Preferably, the reaction temperature of reaction (M1-reac) is from −10 to 250° C., more preferably from 0 to 200° C., even more preferably from 10 to 180° C.

The reaction (M1-reac) can be done in a system, that is closed or open to the atmosphere; preferably the reaction (M1-reac) is done in a closed system.

In a closed system, the pressure depends mainly on the boiling point of the solvent (M-solv), on the amount of ammonia used, and on the reaction temperature of reaction (M1-reac);

preferably, the reaction (M1-reac) is done at a pressure of from atmospheric pressure to 20 bar, more preferably of from atmospheric pressure to 10 bar, even more preferably of from atmospheric pressure to 5 bar.

Preferably, the reaction time of reaction (M1-reac) is from 30 min to 72 h, more preferably from 30 min to 48 h, even more preferably from 30 min to 24 h. Reaction (M1-reac) may be conducted at a constant temperature, or the temperature may be modified during the progress of the reaction. For instance, the reaction may be run for a certain time at first temperature, and then for a given time at second temperature different from the first temperature;

alternatively, the temperature may be modified continuously during the reaction.

Preferably, from 0.5 to 10 mol equivalents, more preferably from 0.5 to 5 mol equivalents, even more preferably from 0.5 to 3 mol equivalents of reagent (M-reag) are used, the mol equivalents being based on the mol of compound of formula (XXI).

When one or more reagents (M-A) different from ammonia, formamide and ethyl carbamate are used, the total amount of substances different from ammonia, formamide and ethyl carbamate used as reagent (M-A) is preferably from 1.0 to 10 mol equivalents, more preferably from 1.1 to 5 mol equivalents, even more preferably from 1.1 to 3 mol equivalents, the mol equivalents being based on the mol of compound of formula (XXI).

When ammonia, formamide, ethyl carbamate or mixtures thereof are used as reagent (M-A), preferably from 1.0 to 100 mol equivalents, more preferably from 1.1 to 50 mol equivalents, even more preferably from 1.1 to 30 mol equivalents of ammonia, formamide, ethyl carbamate or mixtures thereof are used, the mol equivalents being based on the mol of compound of formula (XXI).

When one or more substances selected from the group ammonia, formamide and ethyl carbamate, and one or more substances different from ammonia, formamide and ethyl carbamate are used as reagent (M-A), the given amounts for ammonia, formamide and ethyl carbamate, and the given amounts for the one or more substances different from ammonia, formamide and ethyl carbamate, add up to the total amount of reagent (M-A); the total amount of reagent (M-A) is preferably from 1.0 to 100 mol equivalents, more preferably from 1.1 to 50 mol equivalents, even more preferably from 1.1 to 30 mol equivalents, the mol equivalents being based on the mol of compound of formula (XXI).

Preferably from 0.01 to 15 mol equivalents, more preferably from 0.02 to 10 mol equivalents, even more preferably from 0.02 to 5 mol equivalents of compound (M-comp) are used, the mol equivalents being based on the mol of compound of formula (XXI).

When reagent (M-A) is not one or more substances selected from the group ammonia, formamide and ethyl carbamate, then preferably from 1 to 15 mol equivalents, more preferably from 1 to 10 mol equivalents, even more preferably from 1 to 5 mol equivalents of compound (M-comp) are used, the mol equivalents being based on the mol of compound of formula (XXI).

Preferably, the amount of solvent (M-solv) is from 0.5 to 20 fold, more preferably from 1 to 20 fold, even more preferably of from 2 to 20 fold, of the weight of compound of formula (XXI).

Preferably, the reaction (M1-reac) is done under inert atmosphere.

When tritylamine is used as reagent (M-A), the product of reaction (M1-reac) may be N-trityl medetomidine and the trityl residue would have to be removed.

Preferably in this case, the method for preparation of compound of formula (XX) comprises a further step (M2); step (M2) is done after step (M1); step (M2) comprises a reaction (M2-reac);

reaction (M2-reac) is the treatment of the product of reaction (M1-reac) with an acid (M-acid detrit). Acid (M-acid detrit) is preferably selected from the group consisting of acetic acid, propionic acid, formic acid, HCl or mixtures thereof.

Acid (M-acid detrit) can be used as an aqueous solution.

Any sequence of the reaction of reagent (M-reag) and of reagent (M-A) with the compound of formula (XXI) in reaction (M1-reac) can be used:

compound of formula (XXI) can first be reacted with reagent (M-reag) and then reagent (M-A) added;

or compound of formula (XXI) can first be reacted with reagent (M-A) and then reagent (M-reag) added;

or compound of formula (XXI) can simultaneously be reacted with reagent (M-reag) and with reagent (M-A), this embodiment is preferably suited for the case that reagent (M-A) and solvent (M-solv) are identical and are formamide, ethyl carbamate or acetamide; preferably formamide.

Preferably, compound of formula (XXI) is first reacted with reagent (M-reag) and then reagent (M-A) added;

or compound of formula (XXI) is simultaneously reacted with reagent (M-reag) and with reagent (M-A).

Step (M1) can therefore be done in three alternatives, the three alternatives are alternative (M1-A1), alternative (M1-A2) and alternative (M1-A3).

Alternative (M1-A1) comprises two consecutive steps, a first step (M1-A1-1) and a second step (M1-A1-2);

step (M1-A1-1) comprises a reaction (M1-A1-1);

reaction (M1-A1-1) is a reaction of compound of formula (XXI) with reagent (M-reag) in the presence of compound (M-comp) in solvent (M-solv);

step (M1-A1-2) comprises a reaction (M1-A1-2);

reaction (M1-A1-2) is a reaction of the reaction product of reaction (M1-A1-1) with reagent (M-A) in solvent (M-solv).

Preferably, the reaction temperature of reaction (M1-A1-1) is from −10 to 250° C., more preferably from 0 to 200° C., even more preferably from 10 to 180° C.

Preferably, the reaction temperature of reaction (M1-A1-2) is from 20 to 250° C., more preferably from 50 to 200° C., even more preferably from 80 to 180° C.

Preferably from 0.01 to 1 mol equivalents, more preferably from 0.02 to 1 mol equivalents, even more preferably from 0.02 to 1 mol equivalents of compound (M-comp) are used in reaction (M1-A1-1), the mol equivalents being based on the mol of compound of formula (XXI).

Reaction (M1-A1-2) can be done in the presence of compound (M-comp).

When reagent (M-A) is not one or more substances selected from the group ammonia, formamide and ethyl carbamate, then reaction (M1-A1-2) is preferably done in the presence of compound (M-comp); preferably from 1 to 15 mol equivalents, more preferably from 1 to 10 mol equivalents, even more preferably from 1 to 5 mol equivalents of compound (M-comp) are used, the mol equivalents being based on the mol of compound of formula (XXI).

After reaction (M1-A1-1), the reaction product of reaction (M1-A1-1) can be isolated by standard methods such as hydrolysis, filtration, evaporation of the volatile components, extraction, washing, drying, concentration, crystallization, distillation, chromatography and any combination thereof, which are known per se to the person skilled in the art.

The reaction product of reaction (M1-A1-1) is the compound of formula (XXIII);

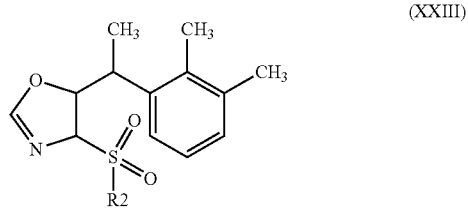

wherein
R2 is 4-tolyl, phenyl, 4-acetamidophenyl, methyl or trifluoromethyl;
preferably, R2 is 4-tolyl, which is compound of formula (23).

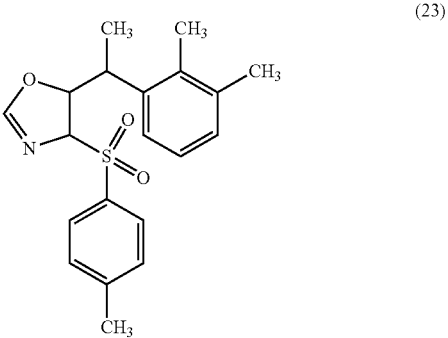 [SMILES: Cc1ccc(S(=O)(=O)C2N=COC2C(C)c2cccc(C)c2C)cc1]

Compound of formula (XXIII) can be isolated after reaction (M1-A1-1) by addition of water to the reaction mixture as obtained from reaction (M1-A1-1). The addition of water precipitates compound of formula (XXIII). Compound of formula (XXIII) can then be isolated by filtration, followed preferably by washing and drying. Compound of formula (XXIII) can be further purified by crystallization.

The volume of water used for this precipitation is preferably from 0.01 to 5 fold, more preferably from 0.05 to 2 fold, of the volume of solvent (M-solv).

Alternative (M1-A2) comprises two consecutive steps, a first step (M1-A2-1) and second a step (M1-A2-2);
step (M1-A2-1) comprises a reaction (M1-A2-1);
reaction (M1-A2-1) is a reaction of compound of formula (XXI) with reagent (M-A) in solvent (M-solv);
step (M1-A2-2) comprises a reaction (M1-A2-2).
reaction (M1-A2-2) is a reaction of the reaction product of reaction (M1-A2-1) with reagent (M-reag) in the presence of compound (M-comp) in solvent (M-solv).

Preferably, the reaction temperature of reaction (M1-A2-1) is from 0 to 250° C., more preferably from 10 to 200° C., even more preferably from 20 to 180° C.

Preferably, the reaction temperature of reaction (M1-A2-2) is from −10 to 250° C., more preferably from 0 to 200° C., even more preferably from 20 to 180° C.

In case of reagent (M-A) not being ammonia and tritylamine, reaction (M1-A2-1) can be done in the presence of an acid (M1-A2-1); acid (M1-A2-1) is selected from the group consisting of p-toluenesulfonic acid, methanesulfonic acid and benzenesulfonic acid;
preferably from 0.01 to 1 mol equivalents, more preferably from 0.05 to 0.5 mol equivalents, even more preferably from 0.1 to 0.3 mol equivalents of acid (M1-A2-1) are used in reaction (M1-A2-1), the mol equivalents being based on the mol of compound of formula (XXI).

Reaction (M1-A2-1) can be done in the presence of compound (M-comp).

When reagent (M-A) is not one or more substances selected from the group ammonia, formamide and ethyl carbamate, then reaction (M1-A2-1) is preferably done in the presence of compound (M-comp); preferably from 1 to 15 mol equivalents, more preferably from 1 to 10 mol equivalents, even more preferably from 1 to 5 mol equivalents of compound (M-comp) are used, the mol equivalents being based on the mol of compound of formula (XXI).

Preferably from 0.01 to 1 mol equivalents, more preferably from 0.02 to 1 mol equivalents, even more preferably from 0.02 to 1 mol equivalents of compound (M-comp) are used in reaction (M1-A2-2), the mol equivalents being based on the mol of compound of formula (XXI).

Alternative (M1-A3) comprises a step (M1-A3-1)
step (M1-A3-1) comprises a reaction (M1-A3-1);
reaction (M1-A3-1) is a reaction of compound of formula (XXI) with reagent (M-reag) and with reagent (M-A) in solvent (M-solv).

Preferably, the reaction temperature of reaction (M1-A3-1) is from 0 to 250° C., more preferably from 20 to 200° C., even more preferably from 50 to 180° C.

Reaction (M1-A3-1) can be done in the presence of compound (M-comp); preferably from 1 to 15 mol equivalents, more preferably from 1 to 10 mol equivalents, even more preferably from 1 to 5 mol equivalents of compound (M-comp) are used in reaction (M1-A3-1), the mol equivalents being based on the mol of compound of formula (XXI).

In case of all these three alternatives, reagent (M-reag), reagent (M-A), compound (M-comp) and solvent (M-solv) are as defined herein, also with all their preferred embodiments.

When the reaction (M1-reac) is completed, the compound of formula (XX) can be isolated by standard methods such as evaporation of volatile components, extraction, washing, drying, concentration, filtration, crystallization, distillation, chromatography and any combination thereof, which are known per se to the person skilled in the art.

Preferably, the volatile components of the reaction mixture are removed by evaporation under reduced pressure.

Preferably, the reaction mixture resulting from reaction (M1-reac) or the reaction mixture resulting from reaction (M2-reac) can be extracted with a solvent (M-extract), solvent (M-extract) is preferably selected from the group consisting of water, toluene, benzene, xylene, chlorobenzene, dichloromethane, chloroform, acetic acid $C_{1-8}$ alkyl ester and combinations thereof;

the acetic acid $C_{1-8}$ alkyl ester is preferably an acetic acid $C_{1-4}$ alkyl ester, more preferably selected from the group consisting of ethyl acetate, isopropyl acetate and butyl acetate;

preferably solvent (M-extract) is selected from the group consisting of toluene, dichloromethane, ethyl acetate, isopropyl acetate and mixtures thereof.

The extraction can be followed by filtration and concentration of the extract.

Preferably, after an extraction with a solvent (M-extract), the extract resulting from the extraction with solvent (M-extract) can be extracted with an aqueous solution of an acid (M-acid). Acid (M-acid) is preferably selected from the group consisting of oxalic acid, citric acid, maleic acid, fumaric acid, tartaric acid, $NH_4Cl$, HCl, HBr, $H_2SO_4$, $H_3PO_4$ and mixtures thereof.

The extract resulting from the extraction with an aqueous solution of acid (M-acid) can be washed with a solvent (M-wash).

Preferably, solvent (M-wash) is selected from the group consisting of toluene, benzene, xylene, chlorobenzene, dichloromethane, chloroform, acetic acid $C_{1-8}$ alkyl ester and mixtures thereof; the acetic acid $C_{1-8}$ alkyl ester is preferably an acetic acid $C_{1-4}$ alkyl ester, more preferably selected from the group consisting of ethyl acetate, isopropyl acetate and, butyl acetate.

The product can be isolated by concentration of the extract that was washed with solvent (M-wash).

In another preferred embodiment, the reaction mixture resulting from reaction (M1-reac) or the reaction mixture resulting from reaction (M2-reac) can be, without above mentioned extraction with solvent (M-extract), acidified by mixing with an aqueous solution of acid (M-acid). The mixture, that is thereby obtained, can be washed with solvent (M-wash), and the product can be isolated by concentration.

If the deprotonated medetomidine is to be isolated, a suspension or solution of the salt of medetomidine, preferably an aqueous suspension or solution of the salt of medetomidine, can be basified by addition of a base (M-basify) or of an aqueous solution of base (M-basify);

preferably base (M-basify) is selected from the group consisting of $NaHCO_3$, $Na_2CO_3$, NaOH and mixtures thereof.

Preferably, base (M-basify) is added in such an amount, that the pH of the resulting mixture is from 7 to 12, more preferably from 8 to 10, even more preferably from 8 to 9.

After the addition of base (M-basify), an aqueous phase can be extracted with solvent (M-extract), followed by isolation of the product by concentration of the extract.

Preferably, any washing of any organic phase after reaction (M1-reac) or after reaction (M2-reac) can be done with water, with base (M-basify), with an aqueous solution of base (M-basify) or with brine.

Preferably, any extraction of any aqueous phase after reaction (M1-reac) or after reaction (M2-reac) is done with solvent (M-extract).

Preferably, the reaction mixture after reaction (M1-reac) or after reaction (M2-reac) is first concentrated under reduced pressure, then diluted with water and acidified with acid (M-acid) as described above, washed with solvent (M-wash), preferably solvent (M-wash) is toluene, basified with base (M-basify), preferably base (M-basify) is an aqueous solution of $NaHCO_3$, and then extracted with solvent (M-extract), preferably solvent (M-extract) is selected from the group consisting of toluene, dichloromethane, isopropyl acetate and ethyl acetate; followed by isolation of the product by concentration of the extract.

In another preferred embodiment, compound of formula (XX) is purified after reaction (M1-reac) or after reaction (M2-reac) by chromatography.

Any organic phase can be dried, preferably over $MgSO_4$ or $Na_2SO_4$.

Any concentration is preferably done by distillation, preferably under reduced pressure.

The compound of formula (XX) can be purified, preferably by crystallization or distillation under reduced pressure, more preferably by crystallization from a mixture of cyclohexane and toluene, even more preferably from cyclohexane:toluene 99:1 v/v.

The compound of formula (XX) may also be converted into a salt by mixing with an acid (M-acid salt), acid (M-acid salt) is preferably used as aqueous solution, acid (M-acid salt) is preferably selected from the group consisting of acetic acid, oxalic acid, HCl and $H_2SO_4$; then it can be isolated by filtration and purified by recrystallization in a solvent (M-cryst), solvent (M-cryst) is preferably selected from the group consisting of water, ethanol, methanol, isopropanol, acetonitrile, hexane, cyclohexane, heptane, toluene, ethyl acetate and mixtures thereof; recrystallization can be repeated using a different solvent (M-cryst).

Preferably, the acidic inorganic solid substance in the list of possible compounds for catalyst (N-cat) is aluminosilicate.

Preferably, the acidic ion exchange resin in the list of possible compounds for catalyst (N-cat) is selected from the group consisting of copolymers of styrene and divinylbenzene and of perfluorinated branched or linear polyethylenes, these polymers being functionalized with $SO_3H$ groups;

more preferably, the acidic ion exchange resin is selected from the group consisting of copolymers of styrene and divinylbenzene containing more than 5% of divinylbenzene, preferably being macroreticular, and of perfluorinated polyethylenes, these polymers being functionalized with $SO_3H$ groups.

Preferably, the inorganic acid in the list of possible compounds for catalyst (N-cat), with which the carbon was treated, is selected from the group consisting of HCl, $H_2SO_4$ and $HNO_3$.

Preferably, catalyst (N-cat) is selected from the group consisting of acetic acid, formic acid, trifluoroacetic acid, methanesulfonic acid, p-toluenesulfonic acid, HCl, HBr, $H_2SO_4$, $H_3PO_4$, $BCl_3$, $BF_3OEt_2$, $MgCl_2$, $MgBr_2$, $AlCl_3$, $ZnCl_2$, $Cu(BF_4)_2$, aluminosilicate, acidic ion exchange resin, carbon treated with HCl, $H_2SO_4$ or $HNO_3$, and mixtures thereof;

more preferably, catalyst (N-cat) is selected from the group consisting of acetic acid, formic acid, methanesulfonic acid, p-toluenesulfonic acid, HCl, $H_2SO_4$, $BF_3OEt_2$, $Cu(BF_4)_2$, aluminosilicate, acidic ion exchange resin, and mixtures thereof;

even more preferably catalyst (N-cat) is selected from the group consisting of methanesulfonic acid, p-toluenesulfonic acid, $H_2SO_4$, $BF_3OEt_2$, $Cu(BF_4)_2$, aluminosilicate, acidic ion exchange resin, and mixtures thereof;

especially catalyst (N-cat) is selected from the group consisting of methanesulfonic acid, p-toluenesulfonic acid, $H_2SO_4$, $BF_3OEt_2$ and mixtures thereof.

Preferably, reaction (N-reac) is done in a solvent (N-solv).

Solvent (N-solv) is preferably selected from the group consisting of water, tert-butanol, isopropanol, acetonitrile, propionitrile, THF, methyl-THF, NMP, dioxane, 1,2-dimethoxyethane, dichloromethane, 1,2-dichloroethane, chloroform, toluene, benzene, chlorobenzene, hexane, cyclohexane, ethyl acetate, acetic acid, formic acid, trifluoroacetic acid and mixtures thereof;

more preferably from water, acetonitrile, propionitrile, THF, 2-methyl-THF, 1,2-dimethoxyethane, dichloromethane, 1,2-dichloroethane, chloroform, toluene, cyclohexane, ethyl acetate, acetic acid, formic acid and mixtures thereof;

even more preferably from water, acetonitrile, propionitrile, THF, 2-methyl-THF, 1,2-dimethoxyethane, dichloromethane, 1,2-dichloroethane, toluene, ethyl acetate and mixtures thereof;

especially from acetonitrile, THF, 2-methyl-THF, dichloromethane, toluene, ethyl acetate and mixtures thereof.

The catalyst (N-cat) can be used in a pure form or as hydrate.

The catalyst (N-cat) can be used as a solution in solvent (N-solv).

Preferably, the molar ratio between catalyst (N-cat) and compound of formula (XXII) is from 1:1000 to 10:1, more preferably from 1:100 to 5:1, even more preferably from 1:50 to 1:1, especially from 1:25 to 1:2.

Preferably, the reaction temperature of reaction (N-reac) is from −20 to 200° C., more preferably from 0 to 150° C., even more preferably from 10 to 100° C.

The reaction (N-reac) can be done in a system that is closed or open to the atmosphere. In a closed system, the pressure depends mainly on the boiling point of a solvent (N-solv) and on the reaction temperature of reaction (N-reac).

Preferably, the reaction (N-reac) is done at a pressure of from 0.01 bar to 20 bar, more preferably of from 0.1 to 10 bar, even more preferably of from atmospheric pressure to 5 bar. More preferably, the reaction (N-reac) is done in an open system.

Preferably, the reaction time of reaction (N-reac) is from 30 min to 72 h, more preferably from 1 h to 48 h, even more preferably from 1.5 h to 24 h.

Alternatively, reaction (N-reac) can be done as a continuous gas-phase reaction by passing the evaporated compound of formula (XXII) over the catalyst (N-cat). This gas-phase reaction can be done in the presence of an inert gas, the inert gas is preferably selected from the group consisting of nitrogen, a noble gas and carbon dioxide.

After reaction (N-reac), compound of formula (XXI) can be isolated by standard methods such as evaporation of volatile components, extraction, washing, drying, concentration, filtration, crystallization, distillation, chromatography and any combination thereof, which are known per se to the person skilled in the art.

Preferably, any volatile components of the reaction mixture or added or generated during work up can be removed by evaporation under reduced pressure.

Preferably, the reaction mixture resulting from reaction (N-reac) or any aqueous phase during the work up after reaction (N-reac) can be extracted with solvent (M-extract), with solvent (M-extract) as defined above, also with all its preferred embodiments.

Preferably, any washing of any organic phase after reaction (N-reac) can be done with water, with a base (M-basify), with an aqueous solution of a base (M-basify), with an aqueous solution of an acid (M-acid) or with brine; with base (M-basify) and acid (M-acid) as defined above, also with all their preferred embodiments.

Any extraction or washing can be followed by filtration and concentration of the extract or of the washed mixture.

In another preferred embodiment, compound of formula (XXI) is purified after reaction (N-reac) by chromatography.

Any organic phase can be dried, preferably over $MgSO_4$ or $Na_2SO_4$.

Any concentration is preferably done by distillation, preferably under reduced pressure.

Compound of formula (XXI) can be obtained in step (N) as the aldehyde as depicted in formula (XXI), but also in form of its hydrate or hemiacetal. The hemiacetal of compound of formula (XXI), which can result as product from step (N), can be the product of an addition reaction between the aldehyde as depicted in formula (XXI) and an alcohol selected from the group consisting of tert-butanol and isopropanol, or between the aldehyde as depicted in formula (XXI) and any alcohol which is used during the isolation after reaction (N-reac). Also this hydrate and this hemiacetal can be directly used in step (M1).

When compound of formula (XXI) is obtained from reaction (N-reac) in form of its hydrate or of a hemiacetal, the hydrate or the hemiacetale can be converted into the aldehyde by standard reactions known to the person skilled in the art.

In another preferred embodiment, compound (XXI) is not isolated after reaction (N-reac). Preferably, reaction (N-reac) and reaction (M1-reac) are done in the same pot. More preferably, after reaction (N-reac) solvent (N-solv) is removed by evaporation, and reaction (M1-reac) is done after evaporation of solvent (N-solv) and in the same pot as reaction (N-reac).

Preferably, R1 is Br.

Preferably, reagent (Q1-reag) is selected from the group consisting of lithium, magnesium, aluminum, isopropylmagnesium chloride, isopropylmagnesium bromide, n-butyllithium, sec-butyllithium, tert-butyllithium, and mixtures thereof;

more preferably, reagent (Q1-reag) is selected from the group consisting of lithium, magnesium, isopropylmagnesium chloride, isopropylmagnesium bromide, n-butyllithium and mixtures thereof.

Reaction (Q1-reac) can be done in the presence of a catalyst (Q1-cat); catalyst (Q1-cat) is selected from the group consisting of iodine, 1,2-dibromoethane, $TiCl_4$, $AlCl_3$, $PbCl_2$, $BiCl_3$, LiCl and mixtures thereof.

Preferably, reaction (Q1-reac) is performed in a solvent (Q1-solv).

Preferably, reaction (Q2-reac) is performed in a solvent (Q2-solv).

Preferably, solvent (Q1-solv) and solvent (Q2-solv) are identical or different and independently from each other selected from the group consisting of THF, toluene, heptane, methylcyclohexane, ethylcyclohexane, hexane, 2-methyl-THF, NMP, diethylether, methyl-tert-butylether, methoxycyclopentane, diisopropylether, 2,2,5,5-tetramethyl-THF, 1,2-dimethoxyethane, N,N,N',N'-tetramethyl-1,2-ethylenediamine, 1,4-diazabicyclo[2.2.2]octane, tri $C_{1-4}$ alkyl amine and mixtures thereof;

more preferably from the group consisting of THF, toluene, heptane, hexane, 2-methyl-THF, 1,2-dimethoxyethane, methyl-tert-butylether, methoxycyclopentane, tri $C_{1-4}$ alkyl amine and mixtures thereof;

even more preferably from the group consisting of THF, toluene, heptane, hexane, 2-methyl-THF, 1,2-dimethoxyethane, triethylamine and mixtures thereof.

When heptane is used as solvent, it is often used as a mixture of isomeric heptanes.

In one particular embodiment, solvent (Q1-solv) is THF, hexane or a mixture thereof, and solvent (Q2-solv) is THF, hexane, toluene or a mixture thereof.

In another particular embodiment, solvent (Q1-solv) and solvent (Q2-solv) are identical. The reaction temperatures of reaction (Q1-reac) and of reaction (Q2-reac) are identical or different and independently from each other preferably from −100 to 150° C., more preferably from −90 to 100° C., and even more preferably from −80 to 80° C.

Reaction (Q1-reac) and reaction (Q2-reac) can be done at a constant temperature, or the temperature may be modified during the progress of the reactions. For instance, the reactions can run for a certain time at first temperature, and then for a subsequent time at a second temperature different from the first temperature. Alternatively, the temperature may be modified continuously during the reaction.

The reaction times of reaction (Q1-reac) and of reaction (Q2-reac) are identical or different and independently from each other preferably from 30 min to 48 h, more preferably from 1 to 24 h, even more preferably from 2 to 12 h.

The amounts of solvent (Q1-solv) and of solvent (Q2-solv) are identical or different and independently from each other preferably from 2 to 40 fold, more preferably from 3 to 20 fold, even more preferably from 5 to 10 fold, of the weight of compound of formula (XXV) in case of solvent (Q1-solv), and of the weight of the reaction product of reaction (Q1-reac) in case of solvent (Q2-solv).

Preferably, from 1.0 to 10 mol equivalents, more preferably from 1.1 to 5 mol equivalents, even more preferably from 1.1 to 3 mol equivalents of reagent (Q1-reag) are used, the mol equivalents being based on the mol of compound of formula (XXV).

Preferably, from 1.0 to 10 mol equivalents, more preferably from 1.1 to 5 mol equivalents, even more preferably from 1.1 to 3 mol equivalents of chloroacetone are used, the mol equivalents being based on the mol of compound of formula (XXV).

Preferably, reaction (Q1-reac) and reaction (Q2-reac) are done at atmospheric pressure.

Preferably, reaction (Q1-reac) and reaction (Q2-reac) are done under inert atmosphere.

Preferably, the inert atmosphere is achieved by the use if an inert gas preferably selected from the group consisting of argon, another noble gas, lower boiling alkane, nitrogen and mixtures thereof.

The lower boiling alkane is preferably a $C_{1-3}$ alkane, i.e. methane, ethane or propane.

After reaction (Q2-reac), compound of formula (XXII) can be isolated by standard methods such as evaporation of volatile components, extraction, washing, drying, concentration, crystallization, distillation, chromatography and any combination thereof, which are known per se to the person skilled in the art.

Preferably, the reaction product of reaction (Q1-reac) is not isolated.

Preferably, reaction (Q1-reac) and reaction (Q2-reac) are done consecutively.

Preferably, reaction (Q1-reac) and reaction (Q2-reac) are done in one pot.

In another preferred embodiment, reaction (Q1-reac) and reaction (Q2-reac) can be done in one pot by adding reagent (Q1-reag) to a mixture of compound of formula (XXV) and chloroacetone in a solvent (Q1-solv).

Preferably, for the isolation of compound of formula (XXII) after reaction (Q2-reac), a reagent (Q3) is combined with the reaction mixture derived from reaction (Q2-reac); reagent (Q3) is selected from the group consisting of water, methanol, ethanol, oxalic acid, citric acid, $NH_4Cl$, HCl, HBr, $HNO_3$, $H_2SO_4$, $H_3PO_4$, acetic acid, propionic acid, formic acid and mixtures thereof.

Preferably, reagent (Q3) is water or aqueous $NH_4Cl$; more preferably, reagent (Q3) is water.

Preferably, from 0.01 to 1000 mol equivalents, more preferably from 0.02 to 1000 mol equivalents, of reagent (Q3) are used, the mol equivalents being based on the mol of compound of formula (XXV). Reagent (Q3) is used to neutralize any excess of reagent (Q1-reag), therefore the amount of reagent (Q3) is adjusted with respect to the excess of reagent (Q1-reag) used in reaction (Q1-reac).

Compound of formula (XXII) is preferably isolated using conventional methods, such as evaporation of volatile components, hydrolysis and optional acidification of the higher-boiling residue, extraction, and distillation.

The compound of formula (XXII) can be purified, preferably by crystallization or distillation under reduced pressure.

Any extraction of an aqueous phase is done preferably with a solvent (Q-extract), solvent (Q-extract) is benzene, toluene, ethyl acetate or isopropyl acetate.

Any organic phase can be dried, preferably with magnesium sulphate.

Any concentration is preferably done by distillation, preferably under reduced pressure.

Compounds of formula (XX), (XX-T), (XXI), (XXII), (XXIII) and (23) are chiral compounds, and the formulae comprise any enantiomer as well as any mixture of enantiomers of the compounds of formula (XX), of formula (XX-T), of formula (XXI), of formula (XXII), of formula (XXIII) or of formula (23) respectively.

Enantiomers can be separated by conventional procedure known in organic chemistry, such as repeated crystallizations of the (+) tartaric acid salt in alcoholic media, as disclosed for compound of formula (XX) in Cordi et al., Synth. Commun. 1996, 26, 1585-1593.

Compounds of formula (XXV) are known compounds and can be prepared according to known methods.

The progress of any of the reactions reaction (M1-reac), reaction (N-reac), reaction (Q1-reac) and reaction (Q2-reac) can be monitored by standard techniques, such as nuclear magnetic resonance spectroscopy (NMR), infrared spectroscopy (IR), High performance Liquid Chromatography (HPLC), Liquid Chromatography Mass Spectrometry (LCMS), or Thin Layer Chromatography (TLC), and work-up of the reaction mixture can start, when the conversion of the starting material exceeds 95%, or when no more starting material can be detected. The time required for this to occur will depend on the precise reaction temperature and the precise concentrations of all reagents, and may vary from batch to batch.

In general, any organic phase can be dried, preferably over $MgSO_4$ or $Na_2SO_4$, if not stated otherwise.

Further subject of the invention is a compound of formula (XXIII).

Further subject of the invention is a compound of formula (23).

Further subject of the invention is the use of compound of formula (XXIII) for the preparation of compound of formula (XX).

Further subject of the invention is the use of compound of formula (XXI) for the preparation of compound of formula (XXIII) or for the preparation of compound of formula (XX).

Further subject of the invention is the use of compound of formula (XXII) for the preparation of compound of formula (XXI).

Further subject of the invention is the use of compound of formula (XXV) for the preparation of compound of formula (XXII).

Compared to prior art, the method of the present invention offers several advantages: Importantly, the whole carbon framework of compound of formula (XX) is built in few chemical steps, using cheap reagents only. The few chemical steps obviously provide for a cost effective procedure. No protecting groups are needed and the overall amount of material used is therefore reduced, the batch size based on molar amounts is increased.

In particular no trityl or acetale protection groups are used and no protection of the imidazoles is necessary. Thereby the number and amount of reagents needed is reduced, and no protecting or deprotecting steps being needed the waste is reduced, contrary to when for example a trityl or acetale protecting group is used. The method has good yields.

EXAMPLES

Methods $^1$H and $^{13}$C NMR spectra were recorded on a Varian VNMRS 500 (500 MHz for $^1$H and 125 MHz for $^{13}$C) instruments in CDCl$_3$. Chemical shifts are expressed in parts per million referred to TMS and coupling constants (J) in Hertz.

EI means Electron ionization mass spectra (70 eV), they were obtained on an AMD-604 spectrometer.

ESI means Electron spray ionization mass spectra

In example 1 the THF was not dried with sodium. In example 2 NaH was used for this purpose.

Example 1

2-(2,3-Dimethylphenyl)methyloxirane, Compound of Formula (XXII), Metallation with Butyllithium in THF To a solution of 1-bromo-2,3-dimethylbenzene (0.27 ml, 2.0 mmol) in THF (4.0 ml) at −78° C. was added n-butyllithium (2.0 ml of a 1.6 M solution in hexane, 3.2 mmol). The mixture was stirred at −78° C. for 30 min, and then a solution of chloroacetone (0.24 ml, 3.0 mmol) in toluene (0.42 ml) was added drop wise within 20 min. The mixture was stirred at −78° C. for 1 h, and then allowed to warm to room temperature. Analysis of a sample after 3 h at room temperature indicated that the title epoxide was the main reaction product. After stirring at room temperature for 3 days the mixture was poured into water (20 ml), and the product was extracted with ethyl acetate (1×10 ml, 2×5 ml). The combined extracts were dried with MgSO$_4$, and concentrated under reduced pressure to yield the title epoxide as an oil in quantitative yield.

$^1$H NMR: 1.59 (s, 3H), 2.28 (s, 3H), 2.31 (s, 3H), 2.83 (br d, J=5.4, 1H), 2.98 (d, J=5.4 Hz, 1H), 7.08 (m, 2H), 7.21 (m, 1H).

MS (EI): 162, 147, 133, 117 (100).

Example 2

2-(2,3-Dimethylphenyl)methyloxirane, Compound of Formula (XXII), Metallation with Magnesium in THF To a suspension of magnesium (89 mg, 3.66 mmol) in THF (4.0 ml) were added NaH (81 mg, 60% in oil, 2.0 mmol), and after stirring at room temperature for 10 min, 1-bromo-2,3-dimethylbenzene (0.40 ml, 2.96 mmol). An exothermic reaction ensues, and the resulting mixture is stirred at room temperature for 1 h. The mixture is then cooled to −20° C., and a solution of chloroacetone (0.26 ml, 3.3 mmol) in toluene (0.63 ml) is drop wise added within 10 min. The mixture is then stirred at room temperature for 2 h. A sample was worked up by mixing with water, extraction with ethyl acetate, and evaporation of the ethyl acetate with a stream of nitrogen. Analysis of the residue by 1H NMR indicated it to be a mixture of xylene and the title oxirane.

Example 3

2-(2,3-Dimethylphenyl)propanal, Compound of Formula (XXI)

2-(2,3-Dimethylphenyl)methyloxirane, compound of formula (XXII), prepared according to example 1 (158 mg, 0.97 mmol), was dissolved in toluene (1.57 mL) and BF$_3$OEt$_2$ (0.006 ml, 0.05 mmol) was added at room temperature. After 2 h at room temperature, a sample was mixed with solid NaHCO$_3$, filtered, concentrated under reduced pressure, and the residue was analyzed by 1H NMR. The crude product consisted essentially of pure 2-(2,3-dimethylphenyl)propanal.

$^1$H NMR: 1.40 (d, J=7.1 Hz, 3H), 2.25 (s, 3H), 2.32 (s, 3H), 3.89 (qd, J=7.1, 1.0 Hz, 1H), 6.89 to 6.92 (m, 1H), 7.12 (m, 2H), 9.67 (d, J=1.0 Hz, 1H).

Example 4

5-(1-(2,3-dimethylphenyl)ethyl)-4-tosyl-4,5-dihydrooxazole, Compound of Formula (23)

To a solution of compound of formula XXII (2.07 g, 12.8 mmol) in dichloromethane (10 ml) was added BF$_3$OEt$_2$ (0.1 molar in Et$_2$O, 4 ml, 0.4 mmol) within 4 h at room temperature. The mixture was stirred at room temperature for 1 h, and the solvent (dichloromethane) was then evaporated under reduced pressure. The residue was dissolved in methanol (10 ml), and TosMIC (toluenesulfonylmethylisocyanide; 2.24 g, 11.5 mmol) and then Na$_2$CO$_3$ (102 mg, 0.96 mmol) were added. The mixture was stirred at room temperature for 1 h, and then diluted with water (5 ml). The mixture was stirred at room temperature for further 30 min, and then kept at 4° C. overnight. Filtration and drying yielded 3.1 g (75%) of compound of formula (23).

$^1$H NMR (CDCl$_3$, 500 MHz): 1.28 (d, J=7 Hz, 3H), 2.23 (s, 3H), 2.30 (s, 3H), 2.44 (s, 3H), 3.28 (m, 1H), 4.79 (m, 1H), 5.20 (m, 1H), 7.04 (s, 1H), 7.10 (m, 3H), 7.33 (d, J=8 Hz, 2H), 7.73 (d, J=8 Hz, 2H).

Example 5

Medetomidine, Compound of Formula (XX)

Compound of formula (23) (3.16 g, 8.84 mmol), prepared according to example 4, was dissolved in ammonia-saturated ethanol (40 ml, containing approximately 160 mmol ammonia) and heated to 110° C. for 3 h. The mixture was then evaporated to dryness, and the residue was mixed with an aqueous, saturated solution of NaHCO$_3$ (20 ml). The mixture was extracted with toluene (2×20 ml), and the combined extracts were washed with water (2×20 ml). The combined extracts were then extracted with 10% aqueous HCl (3×20 ml), and the combined acidic extracts were basified with gaseous ammonia, and extracted with toluene (2×20 ml). The combined organic extracts were dried over Na$_2$SO$_4$, and concentrated under reduced pressure, to yield compound of formula (XX) (1.57 g, 89%).

$^1$H NMR: 1.56 (d, J=7.2 Hz, 3H), 2.18 (s, 3H), 2.25 (s, 3H), 4.35 (q, J=7.2 Hz, 1H), 6.66 (s, 1H), 6.93 (dd, J=6.6, 2.2 Hz, 1H), 6.99 to 7.05 (m, 2H), 7.30 (d, J=1.1 Hz, 1H), 9.84 (broad s, 1H).

$^{13}$C NMR: 14.65, 20.72, 20.88, 14.12, 117.61, 124.62, 125.53, 127.91, 134.05, 134.60, 136.76, 141.11, 143.23.

MS (ESI): 201 [M+H]$^+$

This product was redissolved in acetonitrile (10 ml), and converted into a hydrochloride salt with concentrated aqueous hydrochloric acid (0.8 ml). The mixture was concentrated to dryness, and the residue was suspended in diethylether (30 ml), and stirred at room temperature overnight. Filtration and drying under reduced pressure yielded 1.55 g (74%) of compound of formula (XX) as hydrochloride salt.

The invention claimed is:

1. A compound of formula (XXIII),

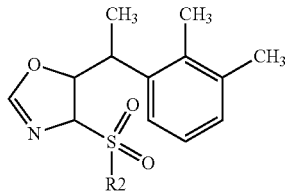

(XXIII)

wherein

R2 is 4-tolyl, phenyl, 4-acetamidophenyl, methyl or trifluoromethyl.

2. The compound according to claim 1, wherein R2 is 4-tolyl.

* * * * *